United States Patent [19]

Egger et al.

[11] Patent Number: 4,919,223

[45] Date of Patent: Apr. 24, 1990

[54] APPARATUS FOR REMOTELY CONTROLLED MOVEMENT THROUGH TUBULAR CONDUIT

[75] Inventors: Shawn E. Egger, 7779 W. Dead Creek Rd., Baldwinsville, N.Y. 13027; Harold G. Sherman, Baldwinsville, N.Y.

[73] Assignee: Shawn E. Egger, Baldwinsville, N.Y.

[21] Appl. No.: 328,685

[22] Filed: Mar. 27, 1989

Related U.S. Application Data

[63] Continuation-in-part of Ser. No. 144,118, Jan. 15, 1988, abandoned.

[51] Int. Cl.[5] .............................................. B62D 57/02
[52] U.S. Cl. ..................................... 180/8.1; 358/100
[58] Field of Search .......................... 180/8.1, 8.5, 8.6; 358/100

[56] References Cited

FOREIGN PATENT DOCUMENTS 85085   5/1985   Japan ................................... 180/8.1
241282 10/1986  Japan ................................... 180/8.1

*Primary Examiner*—Mitchell J. Hill
*Attorney, Agent, or Firm*—Charles S. McGuire

[57] ABSTRACT

Apparatus for remotely controlled movement through linear and curved sections of a pipe, or other tubular conduit. The apparatus includes a pair of members spaced apart along a common, central axis. Each member carries a plurality of extensible and retractable pneumatic cylinders for movement of frictional engagement elements into and out of engagement with the interior wall of the pipe. One or more axial drive cylinders rigidly connect the spaced members for movement thereof toward and away from one another. The apparatus carries equipment for inspecting, measuring and-/or performing other operations on the pipe, and is of simple and economical design, requiring no gimbal joints or other special linkages for movement in the intended manner.

10 Claims, 3 Drawing Sheets

APPARATUS FOR REMOTELY CONTROLLED MOVEMENT THROUGH TUBULAR CONDUIT

REFERENCE TO RELATED APPLICATION

This is a continuation-in-part of U.S. application Ser. No. 144,118, filed Jan. 15, 1988, now abandoned.

BACKGROUND OF THE INVENTION

The present invention relates to apparatus for controlled movement through an elongated tubular conduit and, more specifically, to apparatus for remotely controlled, stepped movement through a pipe to perform inspections, measurements, and/or other operations within the pipe.

Piping such as that used in nuclear power generating facilities, as well as in other applications, must be inspected prior to use and periodically thereafter to determine whether cracks or flaws are present, e.g., at welded locations, which could indicate an actual or potential hazardous condition. It is desirable that means be provided for transporting inspection apparatus, such as a television camera for performing visual inspections on a remote monitor, through the piping. The transporting apparatus may carry equipment in addition to the camera for assisting in visual or ultrasonic inspection, and/or for performing other operations, such as welding or grinding, within the piping.

Pat. No. 4,615,728 disclosesd apparatus including a carriage mounted on wheels for movement through the interior of elongated piping to assist in visual inspection thereof. Another form of apparatus for movement through linear and curved sections of piping to permit visual inspection and other operations to be performed therein is disclosed in U.S. Pat. No. 4,460,920, of Weber et al. and Japanese Pat. No. 60-85085, of Yemaji. The apparatus of these patents includes two stepping mechanisms having parts moveable into and out of gripping engagement with the inside walls of the piping, and drive means for axial movement of the two mechanisms through the pipe. The stepping mechanisms are connected by further structure including at least one gimbal-type joint to permit articulated relative movement of the two spaced stepping mechanisms. The axial drive means may comprise an extensible and retractable cylinder and piston connected between one of the stepping mechanisms and the structure carrying the gimbal-type joint which, in any event, is necessary in order to permit movement of the apparatus through curved sections of piping.

It is a principal object of the present invention to provide novel and improved apparatus for remotely controlled movement through elongated piping for the purpose of performing visual inspection and/or other operations therein.

A further object is to provide apparatus for stepping-type movement through both linear and curved sections of cylindrical piping with two spaced stepping members having portions movable into and out of engagement with the pipe wall, wherein the stepping members are rigidly connected by an axial drive cylinder, thereby simplifying and economizing the design and manufacture of the apparatus, as well as improving performance and reliability.

Other objects will in part be obvious and will in part appear hereinafter.

SUMMARY OF THE INVENTION

In accordance with the foregoing objects, the invention contemplates an internal pipe inspection apparatus including a pair of stepping members each having a plurality of cylinders with extensible and retractable operating rods arranged radially about a common central axis. The two stepping members are separated and movable relative to one another along the central axis by an additional cylinder having portions rigidly attached at opposite ends to portions of the two stepping members. In the preferred embodiment, each of the two stepping members includes a rigid frame of somewhat smaller outer dimensions that the inside diameter of the pipe in which the apparatus is to be used with a plurality of double-acting, pneumatic cylinders fixedly mounted between the frame and a support at the axial center thereof.

The cylinders are mounted at equal angles from one another about the central axis of the frame, with the operating rods extending from the pistons through portions of the frame. Friction feet on the ends of the rods grip the internal surface of the pipe when the rods are extended. All cylinders of each stepping member are actuated for simultaneous extension and retraction of the operating rods. The apparatus may be moved through the pipe in step fashion by retracting the operating rods of one stepping member while those of the other stepping member are extended, in frictional contact with the pipe wall, and actuating the axial drive cylinder to effect relative axial movement of the stepping members.

A combination of features permits movement of the apparatus around elbows or through other curved sections of the pipe. The axial drive cylinder is bolted or otherwise rigidly affixed at one end to the frame of one of the stepping members, and the end of the piston rod is rigidly attached to the frame of the other stepping member. A pair of skids is affixed to the frame on opposite sides of the end of each cylinder from which the operating rod extends. The skids have edge portions farther from the center of the frame than the outer surfaces of the friction feet when the piston rods are retracted. As the apparatus enters a curved section of the pipe and the axial drive cylinder piston rod is extended, the skids on one side of the forward stepping member contact and travel along the pipe surface. This produces some slippage of the friction feet of the rear stepping member on the pipe surface, resulting in some pivoting movement of the entire apparatus within the pipe. The contact area and coefficient of friction between the friction feet and the pipe wall relative to the outward force exerted by the pistons of the stepping members is chosen to ensure that such pivoting movement occurs. Also, the action of the pneumatic cylinders and stroke of the pistons is such that when the stepping members are not centered in the pipe, as when traveling around a curved section, one or more of the operating rods may extend further out of its cylinder than the other(s). That is, the operating rod carrying the friction foot on the side nearest the pipe wall will not extend as far as the operating rod on the opposite side. Repeated movement of the stepping member and axial drive cylinders in predetermined sequence will result in movement of the apparatus through the curved pipe sections due to rotation of the entire unit by slippage of the friction feet on the pipe wall.

In a further preferred refinement, rather than using a single, axial drive cylinder connecting the stepping members at their centers, a pair of such cylinders are each rigidly connected to the stepping members in parallel relation on opposite sides of the axial centerline for concurrent operation in effecting relative axial movement of the stepping members. A television camera is mounted between the two cylinders, extending along the axial centerline. This arrangement offers the dual advantages of increased rigidity of the overall apparatus, and keeping the television camera in focus as it is scanned around the internal circumference of the pipe.

The foregoing objects and advantages will be better appreciated from a consideration of the accompanying drawings and detailed description of the structural and operational features of the movable inspection apparatus of the invention.

BRIEF DESCRIPTION OF THE DRAWINGS

FIG. 4a-4r are a series of diagrammatic, elevational views showing the sequence of movement of the elements as the apparatus travels through a curved section of piping.

DETAILED DESCRIPTION

Figure 1:
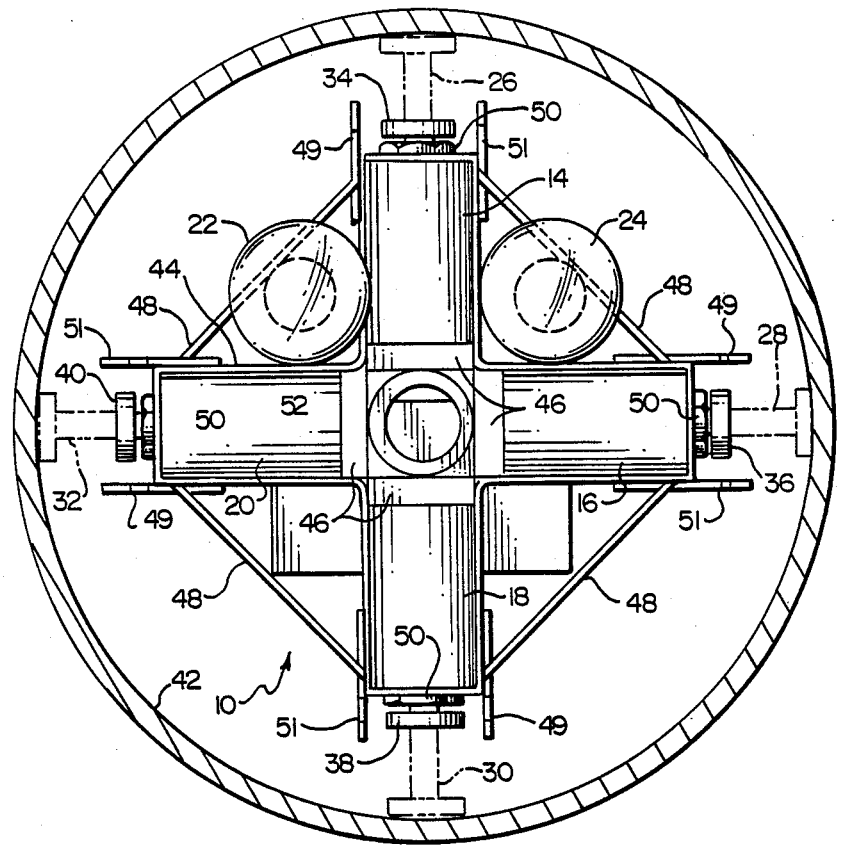
FIG. 1 is a front elevational view of a preferred embodiment of movable inspection apparatus incorporating the features of the present invention, with postions thereof in a second position of movement shown in phantom lines.
Figure 2:
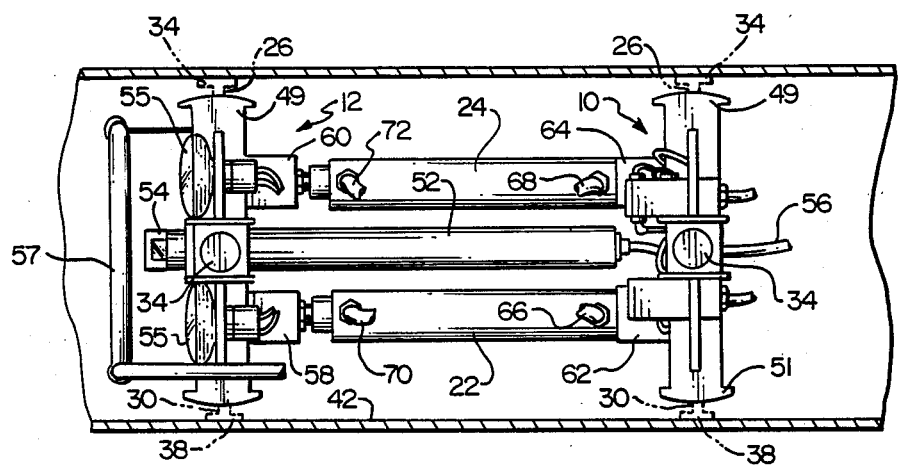
FIG. 2 is a plan view of the apparatus of FIG. 1, with the same portions shown in phantom lines.

Referring now to the drawings, in FIGS. 1 and 2 is shown a preferred embodiment of the apparatus, which includes a pair of spaced stepping members, denoted generally by reference numerals 10 and 12, constructed essentially symmetrically about a central axis. Each of stepping members 10 and 12 includes a plurality of double-acting (i.e., dual ended), pneumatic cylinders; four such cylinders, numbered 14, 16, 18 and 20, are shown in the illustrated embodiment, the minimum practical number in any case being three. Two additional double-acting cylinders 22 and 24 extend between and rigidly join stepping members 10 and 12, parallel to one another and to the axis between the centers of the spaced members.

Pneumatic cylinders 14, 16, 18, 20, 22 and 24 are of conventional design, each having a piston mounted for reciprocating movement within the cylinder portion, and a rod connected to the piston and extending through one end of the cylinder. Piston rods 26, 28, 30 and 32 are shown in FIG. 1 in phantom lines, extending from cylinders 14, 16, 18 and 20, respectively. When so extended, friction feet 34, 36, 38 and 40 on the ends of rods 26, 28, 30 and 32, respectively, engage the inside surface of circular cross-section pipe 42. Each of the cylinders is provided with a fitting connected to a source of pressurized air at both ends, such mechanisms and the controls therefor being conventional and therefore not shown in the present drawings.

Stepping members 10 and 12 include a rigid framework upon which the four cylinders of each member are mounted. The frame of member 10 is seen in FIG. 1, that of member 12 being of the same or similar construction. Frame member 44 extends along both sides and over the outer ends of all four cylinders, and is welded or otherwise fixedly attached to four-sided center support 46. Intermediated braces 48 extend diagonally between and are welded to outer end portions of frame member 44. Skids 49 and 51 are also fixedly attached to the outer frame member portions on opposite sides of the outer end of each of cylinders 14, 16, 18 and 20. The outer edges of skids 49 and 51 are curved, as seen in FIG. 2, and are positioned farther from the centers of stepping members 10 and 12 (i.e., closer to the pipe wall) than friction feet 34, 36, 38 and 40 when rods 26, 28, 30 and 32 are retracted. Threaded fittings on each of the cylinders extend through openings in the portions of frame member 44 which pass over the ends of the cylinders and are secured by nuts 50. In addition or alternatively to the threaded fittings and nuts, cylinders 14, 16, 18 and 20 may be attached by screws extending through the frame member and into the cylinders.

Television camera 52, of commercially available form, is mounted between members 10 and 12, preferably extending along the central axis between the two so that, as scanning mechanism 54 is rotated to reflect an image of the internal circumference of pipe 42 to the camera lens, there is no need to re-focus, provided the apparatus is centrally positioned in the pipe. Camera 52 is fixedly attached to and movable with stepping member 12, electrical cable 56 for operating, and relaying video signals from, camera 52, extending loosely through the center of stepping member 10. Lamps 55 are mounted on the frame of stepping member 12 to illuminate the interior of the pipe. "Black light" tube 57 may also be mounted on the frame member for visual inspections employing a spray penetrant in the manner described in earlier-mentioned Pat. No. 4,675,728. Other items, such as ultrasonic transducers, welding and grinding apparatus, etc., may be carried by the apparatus of the invention, but are not shown since the nature and arrangement thereof are entirely optional.

As also seen in FIG. 2, the ends of the piston rods of cylinders 22 and 24 are rigidly connected by brackets 58 and 60, respectively, to stepping member 12, whereas the opposite ends of the cylinders are rigidly attached by brackets 62 and 64 to stepping member 10. Thus, the entire apparatus is rigidly interconnected, the only relatively movable elements being the pistons and the operating rods of the respective cylinders. Air from a pressurized source outside pipe 42 is supplied to one end of cylinders 22 and 24 through tubes 66 and 68, respectively, for extending the piston rods, and to the opposite end through tubes 70 and 72 for retracting the rods.

Figure 3A:
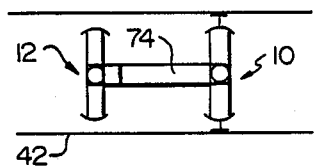
FIGS. 3a-3f are a series of diagrammatic, elevational views showing the sequence of movement of elements of the apparatus in effecting stepped movement through a linear section of piping.

The manner of movement of the apparatus through linear and curved sections of pipe 42 is illustrated in the sequential views of FIGS. 3a-3f and 4a-4r. In FIG. 3a the apparatus is shown with the piston rods of the four cylinders of stepping member 10 extended and those of both the cylinders of stepping member 12 and the axially extending cylinder(s), here denoted by reference numeral 74, retracted. In normal operation the outward force applied by the stepping member cylinders, and the coefficient of friction between the feet on the ends of the operating rods and the inside surface of the pipe, relative to the weight of the apparatus and equipment carried thereby, are such that the portions of the apparatus extending from each stepping member are supported in cantilever fashion when the friction feet of one stepping member are engaged, and those of the other stepping member disengaged, with the pipe surface. That is, the frictional engagement of the feet of one stepping member sill normally support the apparatus both when operating rod(s) 76 of axially extending cylinder(s) 74 is retracted, as in FIG. 3a, and when extended, as in FIG. 3b.

Figure 3B:
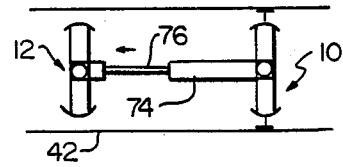
Figure 3C:
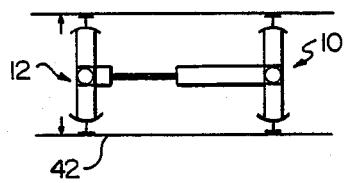
Figure 3D:
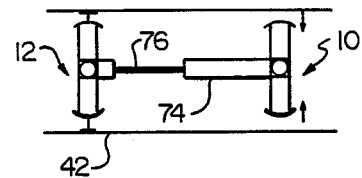
Figure 3E:
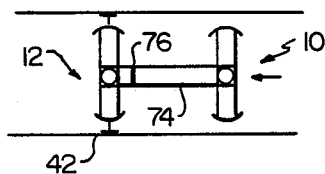
Figure 3F:
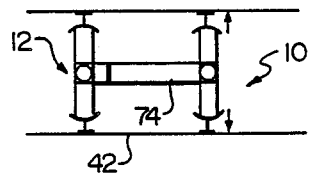

Rod 76 is extended, moving stepping member 12 to the left, i.e., to the position of FIG. 3b. The cylinders of stepping member 12 are then actuated to extend the piston rods thereof, bringing the friction feet into engagement with the inside of pipe 42, as shown in FIG. 3c. The piston rods of the stepping member 10 cylinders aer retracted, as in FIG. 3d, the apparatus then being supported by stepping member 12. Piston rod(s) 76 is then retracted, thereby moving cylinder(s) 74 and stepping member 10 to the right, from the position of FIG. 3d to that of FIG. 3e. Extension of the piston rods of the cylinders of stepping member 10 brings the elements to the position of FIG. 3f, and the steps are then repeated in sequence, resulting in the step-fashion movement of the apparatus through pipe 42.

The same sequence of actuation of the cylinders of stepping member 10 and 12, and of axial drive cylinder(s) 74 is followed in moving the apparatus through a curved section of pipe, denoted in FIGS. 4a–4r by reference numeral 78. The apparatus is shown in FIG. 4a as forward stepping member 10, with the operating rods retracted, approaches the curved section, the operating rods of stepping member 12 being extended and the axial drive cylinder(s) 74 retracted. As cylinder(s) 74 are extended, the apparatus is rotated about an axis transverse to the pipe axis, with skids 49 and 51 adjacent the lower cylinder of stepping member 10 sliding along the pipe surface on the outside of the curve, and friction feet 34 and/or 38 of stepping member 12 slipping on the pipe surface during such rotation. In moving from the position of FIG. 4a to that of FIG. 4b, the lower friction foot on stepping member 12 has slipped from approximately the position indicated at "a" to the illustrated position "b".

The operating rods of the cylinders of stepping member 10 are then extended, with rod 26 of the uppermost cylinder extending further out than rod of the lower cylinder, as seen in FIG. 4c. The rods of the stepping member 12 cylinders are then retracted (FIG. 4d), followed by retraction of axial drive cylinders 74, moving the upper part of stepping member 12 into contact with, or close proximity to the inside of the curve of pipe 78, as seen in FIG. 4e. Thus, when the operating rods of the stepping member 12 cylinders are extended, rod 30 of the lower cylinder extends farther than the rod of the upper cylinder, as illustrated in FIG. 4f.

Upon retraction of the operating rods of the stepping member 10 cylinders, the elements are in the position of FIG. 4g, having taken one complete forward step from the position of FIG. 4a. The same sequence of movement of the cylinder operating rods is then repeated in taking the second complete step, with the apparatus moving through the positions of FIGS. 4g–4m. Again, as cylinders 74 are extended in moving from the FIG. 1g to the FIG. 4h positon, the apparatus rotates as friction foot 38 slips from position "g" to position "j".

A third complete step is illustrated in the sequence of cylinder operations and movements of FIGS. 4m–4r. In moving from the FIG. 4m to the FIG. 4n position, friction foot 38 of rear stepping member 12 slips on the pipe surface from position "m" to position "n." When the apparatus leaves the curved section of pipe and reenters a linear section, in moving from the position of FIG. 4g to that of FIG. 4r, friction foot 38 of forward stepping member 10 slips from position "q" to position "r," and the central axis of the apparatus is again aligned with the pipe axis.

Although the apparatus is shown as completing travel through the curved section in three complete steps, the increments of axial travel of the apparatus may actually be quite small, depending on the radius of pipe curvature. However, movement is possible through curved sections of quite small radius. The length of stroke of the piston of cylinders 74 is proportional to the diameter of the pipe in which the apparatus is to be used, and the radius of the curved sections through which it is expected to travel. For example, a unit designed to operate in 6" diameter pipe may have an axial drive cylinder with a maximum stroke of about one inch, whereas a unit designed to operate in a 10" or 12" pipe with curved sections of larger radii may have a maximum stroke as large as 4".

The stroke of the cylinders on the stepping members should be about twice the distance between the outer surfaces of the friction feet and the pipe wall when the cylinders are retracted and the apparatus is centered in the pipe. That is, when the pipe wall on one side is engaged by skids 49 and 51 on one side, the piston rod on that side will extend only to the extent necessary to bring the friction foot even with the skids; accordingly, the cylinder on the opposite side must extend approximately twice as far in order for the friction foot to engage the pipe as when the apparatus is centered therein. This relationship is illustrated in FIGS. 4a–4r, as the apparatus travels through curved pipe section 78.

The rigidity of the apparatus and the frictional engagement of the feet on the ends of the piston rods of each stepping member with the internal surface of the pipe permit the apparatus to travel both upwardly and downwardly through vertical sections of pipe. Also, the apparatus has no problem in pulling behind it the electric, pneumatic, and any other lines by which various elements of the apparatus are connected to electrical power, compressed air, etc., outside the pipe. The control system is conventional, and is therefore not shown in detail, preferably including solenoid-operated valves for controlling air flow to each end of the stepping member cylinders and the axial drive cylinder.

All four cylinders on each of the stepping members are actuated for simultaneous extension and retraction of the piston rods, and the controls preferably may be selectively actuated either automatically or manually. Although pneumatically operated cylinders are preferred as the means of moving the friction feet into and out of engagement with the pipe surface, solenoid devices with friction feet on the ends of the movalbe plungers could be substituted, if desired. Furthermore, although the apparatus with a plurality of individual friction feet on each stepping member for movement into and out of engagement with the inside surface of the pipe, frictional engagement could be provided by other names, such as inflatable elements surrounding the frame of each stepping member. The invention is based upon the rigid interconnection of three expansion/contraction assemblies, i.e., the front and rear stepping members and the axial drive cylinders. Also, frictional engagement of the expanding and contracting elements on the stepping members with the internal pipe surface relative to the driving force by which the elements are expanded must satisfy two conditions: 1. the engagement of each stepping member must be tight enough to support the remainder of the apparatus in suspended fashion during movement through linear pipe sections which are vertical, and in cantilever fashion during movement through horizontal, linear sections, without significant slippage, and 2. the frictional engagement means must slip on the pipe surface to permit limited rotation of the apparatus about an axis transverse to the pipe axis in response to extension of the axial drive cylinder(s) during movement through curved pipe sections.

What is claimed is:

1. Apparatus for controlled movement through the interior of an elongated, tubular conduit having both linear and curved sections, said apparatus comprising, in combinatin:
    (a) first and second stepping members each including rigid frame disposed about a central axis, and frictional engagement mounted upon said frame and movable with respect thereto between outwardly expanded and inwardly retracted positions relative to said central axis;
    (b) means for moving said frictional engagement means of each of said stepping members between said outwardly extended and retracted positions for frictional engagement with and disengagement from the inside surface of said conduit;
    (c) axial drive means rigidly connecting said first and second stepping members in spaced relation for relative movement along said central axis;
    (d) said axial drive means comprising at least one extensible and retractable member rigidly connected at opposite ends to said rigid frames of said first and second stepping members, respectively; and
    (e) the frictional engagement of said engagement means with said inside surface of said conduit and the forces moving said engagement means to said outwardly extended position and moving said at least one extensible and retractable member to its extended position being such that:
        (i) said frictional engagement of said engagement means of each stepping member will support the remainder of the apparatus in spaced relation to said inside surface of said conduit, without significant slippage, during movement through linear sections of said conduit; and
        (ii) said frictional engagement permits slippage of said engagement means of each stepping member upon said inside surface of said conduit to permit limited rotation of said apparatus about an axis transverse to the axis of said conduit in response to movement of said extensible and retractable member to its extended position during movement through curved sections of said conduit.

2. Apparatus according to claim 1 wherein said axial drive means comprises at least one cylinder having a piston and piston rod movable along a line parallel with said central axis.

3. Apparatus according to claim 2 wherein said cylinder is rigidly connected at one end to said first stepping member, and said piston rod extends from the other end of said cylinder and is rigidly connected to said second stepping member.

4. Apparatus according to claim 1 where said axial drive means comprises a pair of cylinders, each having a piston and a piston rod movable along lines parallel to one another and to said central axis.

5. Apparatus according to claim 4 wherein each of said cylinders is rigidly connected at one end to said first stepping member, and said piston rods extend from the other ends of said cylinders and are rigidly connected to said second stepping member.

6. Apparatus accordong to claim 1 wherein said frictional engagment means comprises a plurality of friction feet affixed to the ends of respective piston rods and said means for moving said engagement means comprise cylinders from which said piston rods extend.

7. Apparatus according to claim 6 wherein said cylinders are mounted upon said rigid frame of each of said stepping members with said piston rods extending radially about said central axis.

8. Apparatus according to claim 7 wherein the number of said cylinders is four.

9. Apparatus according to claim 7 and further including at least one element attached to said rigid frame adjacent each of said feet, said element having an outer portion positioned farther from said central axis than the outermost surface of the adjacent foot when the associated piston rod is fully retracted, whereby said ouuter portion will contact the internal surface of said tubular conduit before said adjacent foot when said stepping member is advanced to cause said contact in a curved section of said conduit.

10. Apparatus according to claim 9 wherein said element comprises a pair of plate-like members affixed to said rigid frame of each of said stepping members and positioned on opposite sides of each of said feet in the fully retracted position of said piston rods.

* * * * *